United States Patent [19]

Cochran et al.

[11] Patent Number: 5,215,521
[45] Date of Patent: Jun. 1, 1993

[54] LAPAROSCOPY ORGAN RETRIEVAL APPARATUS AND PROCEDURE

[76] Inventors: James C. Cochran; Christopher S. Cochran, both of 3500 Greenbrier, Dallas, Tex. 75225; Edwin L. Buckley, 208 Phlox, Lakeway, Tex. 78734

[21] Appl. No.: 799,355

[22] Filed: Nov. 26, 1991

[51] Int. Cl.$^5$ .............................................. A61B 17/00
[52] U.S. Cl. ..................... 604/22; 604/328; 128/DIG. 24; 128/898; 600/37; 606/128; 606/170; 606/172; 606/179; 383/73
[58] Field of Search ............... 600/37; 604/22, 327, 604/328, 356; 606/127, 128, 159, 170, 172, 179; 128/850, DIG. 24, 897, 898; 383/73

[56] References Cited

U.S. PATENT DOCUMENTS

| | | | |
|---|---|---|---|
| 3,526,219 | 9/1970 | Balamuth | 604/22 X |
| 3,863,639 | 2/1975 | Kleaveland | 128/850 |
| 3,945,375 | 3/1976 | Banko | 606/170 X |
| 4,061,146 | 12/1977 | Baehr et al. | 604/22 X |
| 4,553,537 | 11/1985 | Rosenberg | 128/850 |
| 4,729,763 | 3/1988 | Henrie | 606/179 X |
| 4,823,793 | 4/1989 | Angulo et al. | 606/128 |
| 4,867,157 | 9/1989 | McGurk-Burleson et al. | 606/170 |
| 4,867,576 | 9/1989 | Boyd | 383/73 X |
| 5,037,379 | 8/1991 | Clayman et al. | 600/37 |
| 5,074,867 | 12/1991 | Wilk | 606/128 |
| 5,143,082 | 9/1992 | Kindberg et al. | 128/DIG. 24 X |

FOREIGN PATENT DOCUMENTS

| | | | |
|---|---|---|---|
| 25796 | 1/1884 | Fed. Rep. of Germany | 606/127 |
| 1272412 | 8/1961 | France | 606/127 |

Primary Examiner—Randall L. Green
Assistant Examiner—Mary Beth O. Jones
Attorney, Agent, or Firm—Henry Croskell

[57] ABSTRACT

Laparoscopy organ retrieval apparatus and procedures are presented for minimum invasion surgery inclusive of laparoscopic nephrectomy, cholecystectomy and other organ dissection, morsellation removal from the abdomen through a keyhole incision. The apparatus and procedures permit the safe and total removal of an organ from a body cavity in a morsellated condition through the combination utilization of an entrapment envelope sheath. The entrapment envelope having an apparatus for opening and closing, the apparatus controlled from an exterior position of the body cavity wherein the entrapment envelope after entry of the sheath is extruded from the sheath which has been inserted through a laparoscopic port in place in a keyhole surgical opening. The entrapment envelope is constructed of flexible, relatively low bulk fluid impermeable materials having sufficient strength to contain morsellator entry, organ fragmentation and removal.

18 Claims, 6 Drawing Sheets

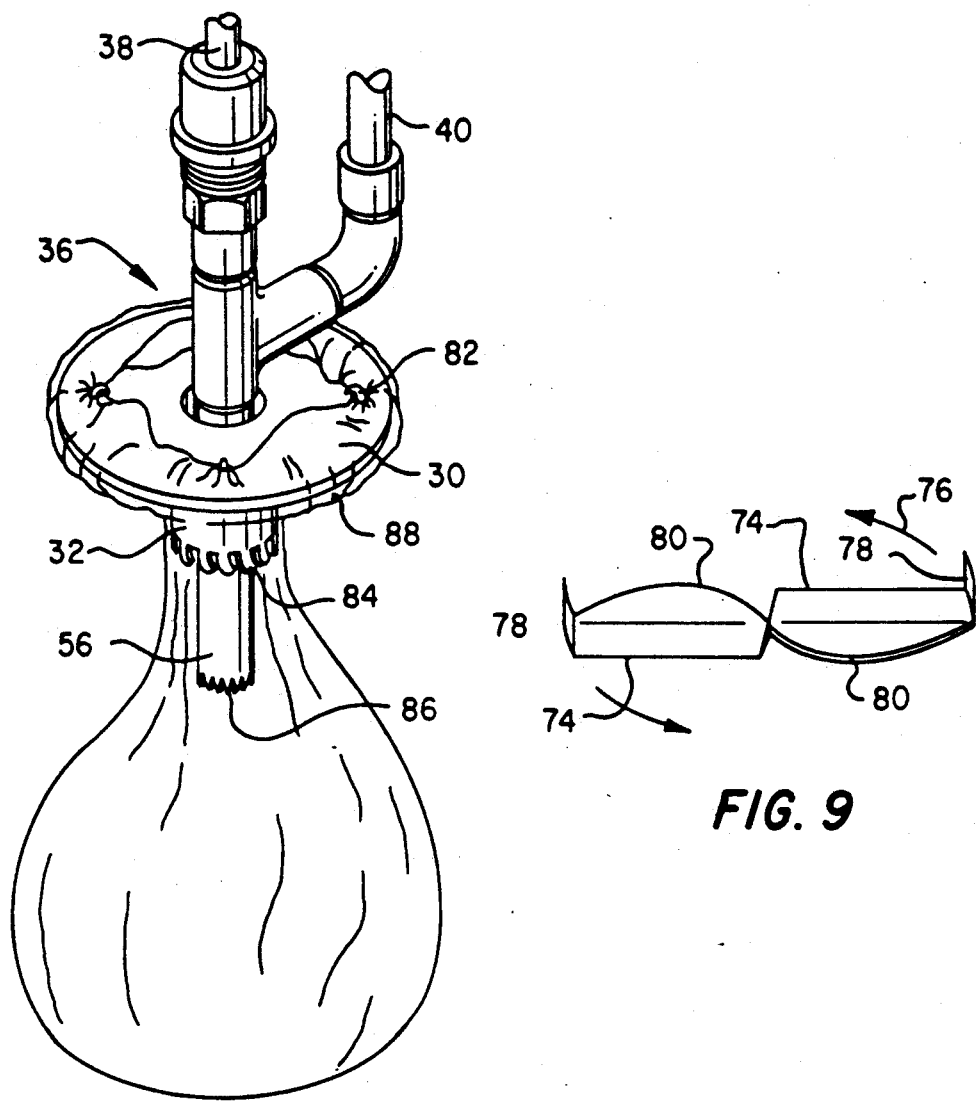
FIG. 10
FIG. 9
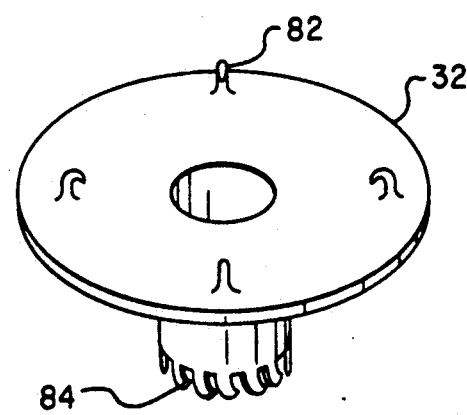
FIG. 11

LAPAROSCOPY ORGAN RETRIEVAL APPARATUS AND PROCEDURE

FIELD OF THE INVENTION

The invention relates to laparoscopic organ retrieval apparati and procedures for minimally invasive surgery dealing with intra-abdominal or other body cavity surgery. In another aspect the invention relates to an improved method and apparatus of organ entrapment and effective fragmentation-evacuation of the dissected and entrapped organ. In yet another aspect, the invention relates to laparascopic organ retrieval apparati and procedures for containment, dissection, morsellation of substantially solid organs such as kidneys utilizing minimal invasive surgery.

BACKGROUND OF THE INVENTION

A multitude of minimally invasive surgical techniques have recently arisen, including such procedures as laparoscopic cholecystectomy and laparoscopic nephrectomy which present significant advances in clinical surgery. Until recently the laparoscopic approach has been limited either to a diagnostic function or to the removal of small amounts of tissue or to thin wall, hollow organs such as the gall bladder and appendix. For example, in laparoscopic cholecystectomy, a miniature TV camera and surgical instruments are inserted through keyhole size punctures in the abdomen. A camera displays the patient's internal organs on a monitor which the surgeon watches while manipulating the surgical tools to dissect and isolate the gall bladder within the abdominal cavity. The possibilities of video surgery or telescopic surgery are not limited to gall bladders since medical procedures have applied such technology to surgical treatment of ulcers, hernias and appendectomies.

Surgical disciplines dealing with minimally invasive surgery addressing intra-abdominal surgery have been impacted by the laparoscope. Laparoscopic procedures for gynecology, for which the laparoscope was originally designed, include removal of small uterine myomata, tubal ligation, and ovariectomy. In general surgery, cholecystectomy, the diagnosis of the acute abdomen, herniorrhaphy, and appendectomy all can be done laparoscopically. In urology, the diagnosis of the cryptochide testicle and more recently pelvic node dissection have been accomplished using a laparoscopic approach.

Laparoscopic cholecystectomy, like open incisional surgery, removes the gall bladder in order to cure gall bladder disease such as gall stones, i.e. pebble size globs of cholesterol that accumulate in the organ and cause painful attacks when they clog certain digestive passageways. Patients who undergo laparoscopic surgery not only endure less pain and scarring, also experience substantially reduced hospital bed recovery time and return to active lives much sooner than patients experiencing open cavity surgery.

Attempts to remove larger solid organs such as kidneys, spleen, liver and uterus, have been frustrated by the lack of a rapid tissue morsellator apparatus, suitable entrapment envelope and methods for manipulating the envelope for receiving and retaining the vigorous morsellation breakup and evacuation of the organ tissue. Unlike the malleable gall bladder, which lies accessible on the liver, the kidney, for example, is solid, and embedded, and in fact entangled in blood vessels. Even with improved morsellators, there are increased risks due to the large solid organs requiring substantially more energy to particularize and evacuate. Possible spillage of infected organ contents or contamination from such organ tissue have stalled the development of laparoscopic approaches principally due to the difficulties of isolating and bagging the removed organ in an entrapment envelope. The strength and quality of the entrapment envelope and its maneuverability remains paramount in the full development of laparoscopic techniques in order to provide sufficient safety expectation which precludes tissue contamination or bacterial spillage into the cavity.

Removal of large solid organs such as kidney laparoscopically, despite recent developments and advances in apparatus, continues to need improvements in tissue dissection, improvements in the method and apparatus for organ entrapment, as well as a means for effective fragmentation and evacuation of the entrapped organ. Laparoscopic equipment for tissue dissection has been the subject of considerable developmental improvement, for example the availability of irrigation/aspiration devices, delicate curved and straight forceps, and an effective multiload clip applier now enables the surgeon to dissect and secure a variety of vascular structures, including the renal vessels. Despite these advancements, two interrelated problems still exist before a large solid organ such as the kidney can be removed in an efficient and safe manner includes organ morsellation and organ entrapment.

Researchers have utilized farm pigs in their various laparoscopic surgical procedures in order to further advance equipment and procedures. A keyhole incision was made in the animal in the midline of the abdomen with insertion of a telescope filled with a miniature TV camera and associated surgical instruments into the abdominal cavity. After appropriate isolation, dissection and clamping of the multiple arteries and veins, the kidney was elevated from its retroperitoneal bed and dissected therefrom, thus being available in the abdominal cavity as a separated, free form organ. A plastic or nylon sack was then introduced into the abdominal cavity using forceps and the like in order to open the mouth of the sack for purposes of inserting into the sack the severed kidney. Various difficulties have arisen in trying to insert and manipulate, i.e. open the sack and previously have required other keyhole entry for special apparatus to perfect the opening and the transfer of the severed kidney into the sack. In some procedures a drawstring on the sack was gathered using forceps in order to close the sack, which is then partially pulled into a sheath. The sheath and related apparatus is then removed from the abdomen, leaving the neck of the sack to be manually grasped upon exit of the skin of the abdomen. With the kidney suspended in the sack and drawn up to the underside of the abdominal wall, the mouth of the sack is reopened in order to attempt to morsellate the kidney in the sack and thereby extract the entire organ in particulate form from the sack and eventually the sack itself. Attempts to morsellate the kidney electrically with an orthopedic drill or available morsellation devices have not been satisfactory. A Cavitron ultrasonic aspirator was used to fragment and aspirate kidneys from a sack, albeit in a very slow procedure. Morsellation devices have been used which can expedite the fragmentation of the organ. However, such morsellation devices present problems regarding the plastic bag, i.e. damage of the bag from the morsellation device, thus spillage and contamination of the abdominal cavity.

Organ entrapment and organ morsellation, especially the large solid organs such as kidneys, spleen, liver and the like, continue to be a concern to the surgeon because of the safety factor as well as surgical procedure complexities and surgical time span. Although manual laparoscopic morsellators are available which are designed predominantly for use with small tissue items, such apparati are not readily suitable for large solid organ morsellation. Other types of electrical or ultrasonic morsellators such as orthopedic drills or ultrasonic surgical aspirators, rely on active suction to help evacuate the fragmented tissue. Such suction has been found to rapidly deplete the $CO_2$ pressurized peritoneum cavity resulting in collapse of the abdominal cavity and loss of visibility.

A recently issued United States patent, U.S. Pat. No. 5,037,379 issued Aug. 6, 1991 entitled Surgical Tissue Bag and Method for Precutaneously Debulking Tissue, provides yet another attempt to overcome some of the procedural and apparatus shortcomings existing in laparoscope organ retrieval technology. The '379 Patent teaches a tissue bag comprised of two layers of materials, an inner layer of a puncture-resistant material and an outer layer of moisture-proof material for containing cells and fluid. The bag material is foldable and flexible for insertion through an access opening into the surgical site. A draw-string is attached to the open end of the bag to close the bag when the tissue is contained therein and pulled through the puncture site in the outer surface of the skin. The bag is bulky in the way it is formed, the two layers comprising a single sheet having opposite first and second ends folded back to contact each end to form a folded side of the bag. The rather stiff fold-back portions along one side and across the bottom as illustrated in FIG. 1A is touted as advantageously causing the open end of the bag to open for receiving tissue once inserted into the body cavity. Such a bulky bag mechanism appears to be cumbersome and awkward in the sense of manipulating the bulk through the keyhole incision as well as manipulation within the body cavity.

In view of these continuing procedural and apparatus shortcomings, the present invention presents an improved laparoscopic organ retrieval apparatus and procedures for entrapping the organ in an impermeable entrapment envelope and means for readily deploying said envelope into the abdominal cavity as well as manipulating the opening of the envelope and the closing of same upon the insertion of the organ. Such means for manipulating the entrapment envelope immediately isolate the diseased tissue from the abdominal contents. In addition, the entrapment envelope is constructed of sufficiently impermeable materials to allow the use of electrical morsellator devices relying on partial suction evacuation and substantial cutter head adaptations which allow for the relatively quick fragmentation and evacuation of the organ. The entrapment envelope must be of a thin, low-bulk material and yet have sufficient strength to withstand high speed motor driven morsellation of solid tissue without perforation of the envelope, thereby precluding seeding of the abdomen with diseased fragments or bacteria from the morsellated tissue.

SUMMARY OF THE INVENTION

The laparoscopic organ retrieval apparatus and procedures according to the invention focus on an organ retrieval system such as the entrapment envelope and the organ morsellator. Body cavity organ retrieval systems which provide minimally invasive surgery methodology permit the safe and total removal of an organ from a body cavity in a fragmented condition through the combination of an entrapment envelope, entrapment envelope sheath and entrapment envelope expansion and manipulation means. Following the detachment of the organ from its connection to the body within the body cavity such as the abdomen, the organ retrieval system entrapment envelope is delivered through a laparoscopy port into the body cavity. The entrapment envelope is arranged with handling means such as wires and wire guides or pneumatic means in the envelope which can be activated once the envelope is in a loosened position from the sheath in the $CO_2$ inflated body cavity; thus allowing the placement of the organ into the opened envelope by appropriate maneuvers. Handling means either through wire mechanisms or pneumatic tubing control manipulations of the envelope then allows for tightening or closing of the envelope in order that the envelope can then be drawn through the keyhole incision by means of the wire extensions or other extensions of the envelope until the neck of the envelope protrudes above the skin level. The neck of the envelope is then slightly open to permit the insertion of an organ retrieval system tissue morsellator. The organ retrieval system tissue morsellator is activated by attaching a suction means to a suction port and attaching a drive means for the morsellator drive shaft and cutting head. A source of vacuum at a head or end portion of the morsellator cutting head greatly assist in allowing cutting contact with the organ without dangerous plunging motions of the morsellator. In the alternative, a hand crank mechanism can be utilized in removing non-solid, smaller tissue organs. Irrigation can also be attached to the system through an irrigation port to aid in the flushing of tissue fragments through the suction device. The suction device and morsellator are activated to morsellate the tissues and when the morsellation of the organ is complete, the envelope and any remaining fragments of tissue are removed through the laparoscopy port. Tissue aspirated through the suction system can be trapped in a tissue trapping container such as a suction cannister. Tissue can then be removed from the trap or container for pathological evaluation.

When the organ to be removed is a solid organ such as a kidney, the morsellator must have the cutting and removal capability for fragmenting and removal of such a solid organ within a reasonable time period while still being of such a nature as not to rupture or damage the entrapment envelope. The entrapment envelope must of course be of highly flexible construction and of substantially low bulk while yet exhibiting substantial strength to avoid any rupturing or tearing by the morsellator during the morsellization process. In addition, the entrapment envelope must be readily insertable into the cavity and pliable as to expansion of the envelope for receiving the organ and closing of the envelope upon receipt of the organ and capable of being drawn through the keyhole incision for control and entry of the morsellation procedure. The low bulk, highly flexible yet perforation resistive entrapment envelope material must be fluid and gas impervious since no body cavity leakage can be tolerated.

BRIEF DESCRIPTION OF THE DRAWINGS

These and other objects of the present invention will be more clearly understood in connection with the accompanying detailed description of the attached drawings in which:

FIG. 9 is an enlarged perspective view in isolation of yet another morsellator cutting head embodiment.

FIG. 10 is an perspective view of the morsellating device in place within the morsellation guide, both being inserted into the entrapment envelope or bag which contains, for example, kidney or other extracted body tissue which will be morsellated and removed from the body cavity. The envelope has been drawn through the surgical keyhole opening and secured to the morsellation guide which utilizes slanted teeth on the inserted tube termination end to hold the tissue from rotating during contact with the rotating morsellator cutters.

FIG. 11 is a top perspective view of the morsellation guide showing inward facing bag fastening hooks and unidirectional slanted teeth on the circumference of the termination portion of the morsellation guide which is inserted into the entrapment envelope or bag.

DETAILED DESCRIPTION OF THE DRAWINGS

Figure 1:
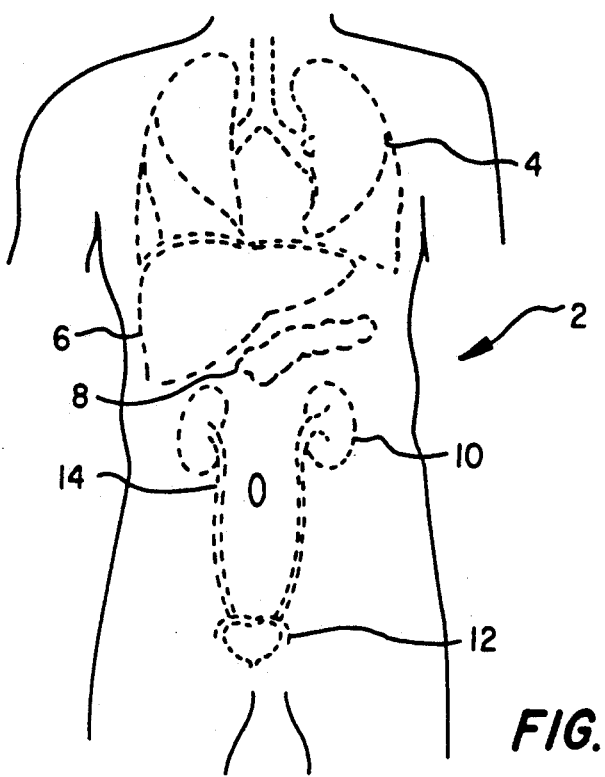
FIG. 1 is a partial front elevational view of a human body with various organs shown in phantom and a surgical keyhole opening suitable for laparoscopic procedures.

Tissue morsellation entrapment envelopes can be of various shapes and sizes and materials depending on the body organs to be retrieved. All envelopes are of fluid and gas impervious materials such as nylon, polyester, cotton, silk, polypropylene, mesh, and like materials which can be laminated, coated on the exterior and/or interior surfaces with further rubberized laminants or plastic coatings. The organ retrieval system in accordance with the present invention combines the use of such envelopes having various handling means for inserting into the body cavity through a sheath for readily opening the entrapment envelope with a mechanism within the body cavity as well as readily closing said envelope after insertion of the severed organ. These entrapment envelopes along with various morsellator cutter heads combined to present an organ retrieval system which can be custom tailored to specific laparoscopic organ retrieval procedures. In one embodiment a tissue morsellator is comprised of a hollow tube of metal, plastic or molded polymer or the like with a tissue envelope guard extending slightly beyond the end of a morsellator cutting means with an aspiration port and irrigation port at the opposite end. The cylindrical tube morsellator can contain a rotary helix for transporting the morsellated organ particles from the cutter head, the proximal end, of the helix to an aspirator at the distal end. The cutter or cutting head can be arranged in a variety of single and double blade apparati utilizing a side port on the morsellator cylindrical end portion. In another embodiment the cutter may be recessed and positioned in an open end of the morsellator cylindrical body utilizing vacuum control for pulling organ tissue into contact with the cutter blade. In yet another embodiment the cutter head is exposed through a side window with the morsellator cylindrical body closed at the end.

The morsellator cylindrical body has supports at the proximal and distal ends for axial support of the helix and the cutter when the side port cutter apparatus is used. The distal end of the morsellator tube has a gas and liquid tight seal and the axis of helix projects far enough for the attachment of a hand crank or motor drive means. The proximal end of the helix, the cutter end, can be provided in one embodiment with a semicircular axial guard which projects 5-10 mm from the end of the tube in order to protect the entrapment envelope and to provide axial support for the helix and cutter. Near the distal end of the morsellator tube is a vacuum discharge for the fragmented organ tissue. Irrigation fluid may be introduced in aid of transport of a morsellated tissue. The vacuum discharge port conducts the morsellated organ into a tissue trapping vacuum chamber. The inlet to the trapping chamber is provided with a mesh bag in which the organ tissue is trapped. This bag and its contents are suitable for removal enabling pathological examination of the tissue particles.

Use procedures of the organ retrieval apparatus involve the collapsed impervious entrapment envelope being introduced into the patient abdomen through a keyhole and a laparoscopic port utilizing a sheath tube which houses the envelope thus avoids damage or contamination of the envelope before introduction to the body cavity. The entrapment envelope is projected into the body cavity and the detached organ is manipulated into an opened entrapment envelope, the envelope being connected to expansion and closure means such as wire guides or pneumatic handling means. The entrapment envelope opening and closing means are comprised of tubular guides defining the circumference of an opened portion of the entrapment envelope, the tubular guides being in communication with the entrapment envelope when the envelope is within the body cavity. The tubular guides being controlled from a position exterior of the body cavity, for example the tubular guides being suitable for receiving a wire member in combination with pneumatic means. In the case of pneumatic tubular means, the entrapment envelope contains such means extending from the entrapment envelope opening circumference to form expansion loops around the perimeter of the unopened portion of the envelope for expanding and opening the envelope. The entrapment envelope can also further utilize tubular staves extending from the entrapment envelope opening circumference to form expansion loops around the parameter of the unopened portion of the envelope. In a related manner the envelope can be closed once the organ is inserted into the envelope and the mouth of the envelope being retrievable through the keyhole incision. The morsellator tube is then inserted into the open neck of the envelope, the envelope being secured for morsellation removal of the organ. In one embodiment the envelope guard at the proximal end of the morsellator tube prevents damage to the envelope and consequently possible abdominal infection as the helix and cutter are rotated to fragment the detached organ. In other morsellator embodiments, other means are employed to safeguard the envelope, for example, vacuum control such that the envelope will not be pulled into the cutter. The helix transports the morsellated organ to the discharge vacuum port where the vacuum, optionally aided by the admission of irrigation fluid, transports the morsellated organ tissue to an organ trapping vacuum container.

For purposes of promoting an understanding of the principles of the invention, reference will now be made to the embodiments illustrated in the drawings and specific language will be used to describe same. It will nevertheless be understood that no limitation of the scope of the invention is hereby intended, as alterations and further modifications of the illustrated device and such further applications of the principles of the invention as illustrated therein being contemplated as would normally occur to one skill in the art to which the invention relates.

Referring to FIG. 1, there is shown a partial front elevational view of a human body with various organs in phantom, said body having a surgical keyhole opening suitable for laparoscopic procedures. The body cavity 2 shows in phantom lungs 4, liver 6, pancreas 8, kidneys 10 and bladder 12. The keyhole body surgical opening 14 provides for minimum invasion surgical techniques utilizing laparoscopy organ retrieval apparatus and procedures. Such procedures allow for example a kidney 10 to be removed surgically through keyhole body surgical opening 14 which is substantially smaller than the dense tissue kidney. Minimum invasion surgical techniques utilizing a keyhole body surgical opening 14 for kidney 10 or gall bladder removal avoids extensive surgical incision lengths and expedites the patient's recovery not only in terms of hospital bed time but also return to active life.

Figure 2:
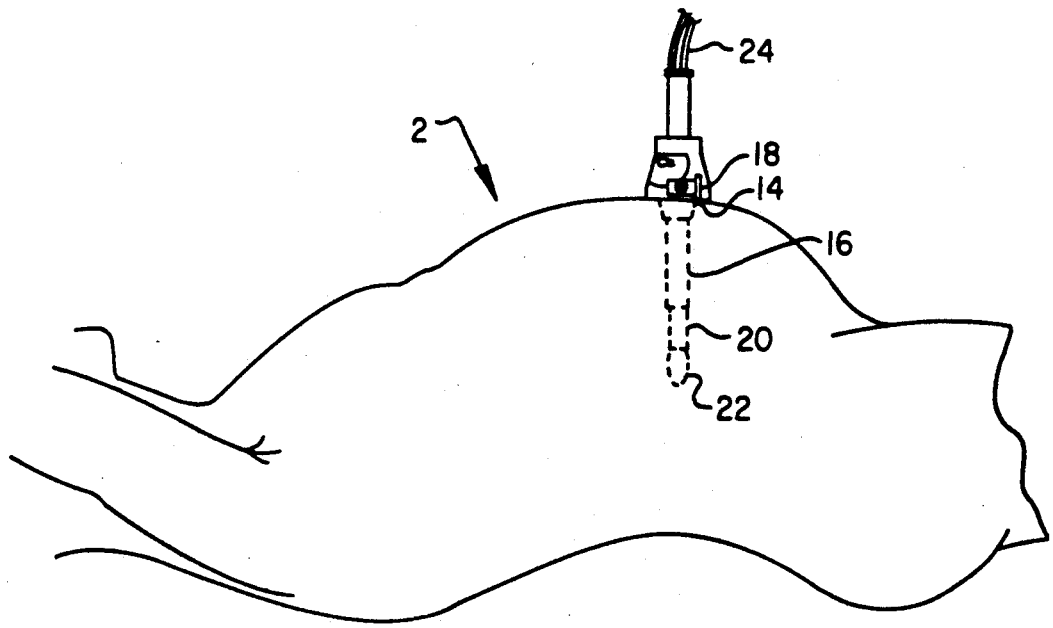
FIG. 2 is a partial side elevational view of a human body with a laparoscopic port and inserted sheath positioned within the body abdominal cavity which has been inflated.
Figures 3, 4:
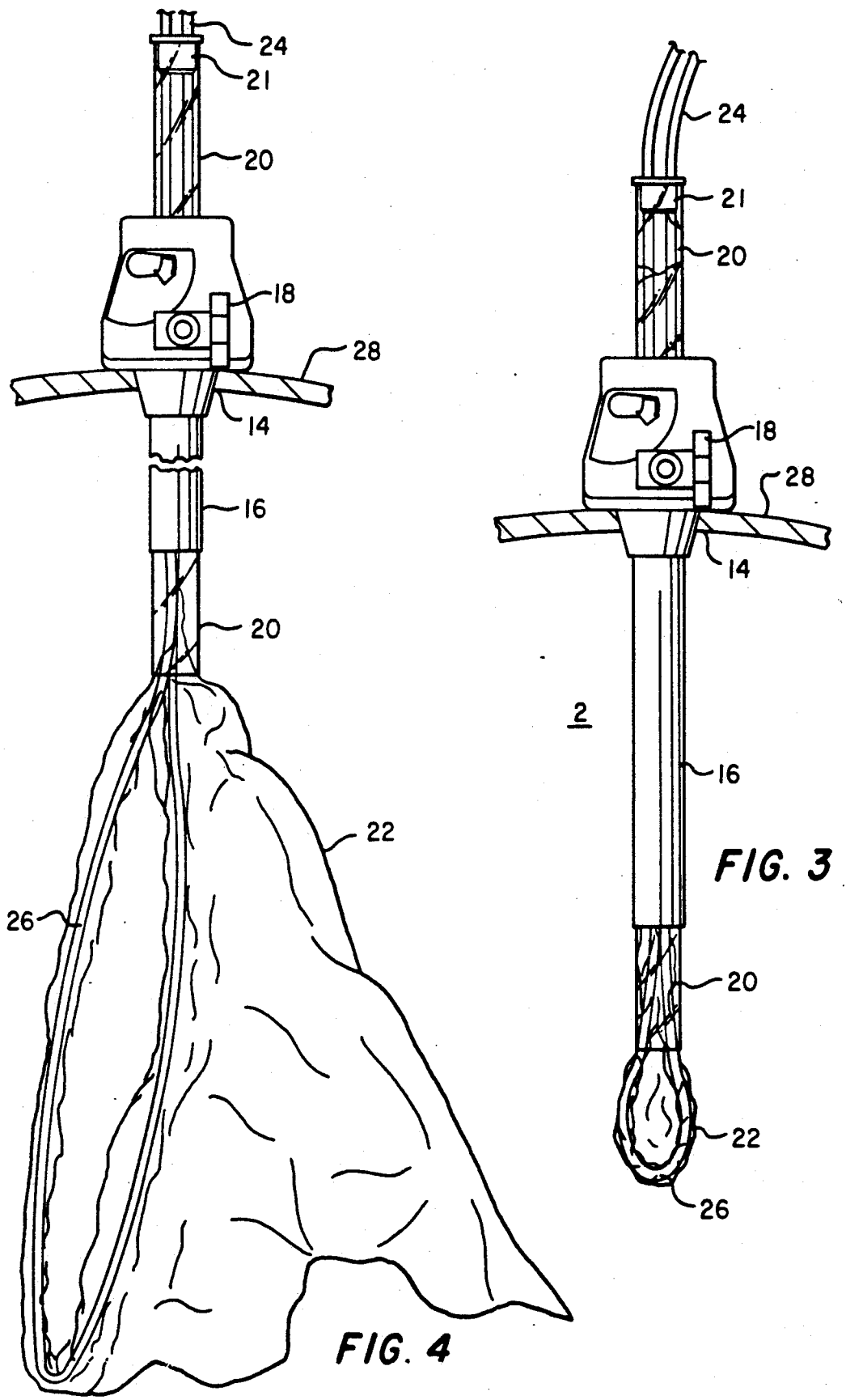
FIG. 3 is an enlarged sectional view of FIG. 2 showing the body skin line only with the sheath inserted in the laparoscopic port and with a portion of the entrapment envelope entering the body cavity through the sheath.
FIG. 4 is an enlarged sectional view in accordance with FIG. 3 with the entrapment envelope being fully inserted into the body cavity and opened for receiving surgically removed body organs.

FIG. 2 presents a partial side elevational view of a human body with a laparoscopic port and sheath inserted therein, both elements being inserted into the body abdominal cavity which has been inflated. The human body cavity 2 which has been inflated by $CO_2$ or some other suitable gas allows use of the laparoscopic port 16 which provides gas pressure means 18 and inflation of the body cavity 2 for purposes of telescope or miniature television and surgical instrument manipulations. Once a body organ has been surgically severed from its body attachments, for example kidney 10, the surgically isolated kidney is held in the body cavity until an entrapment envelope 22 is introduced to the inflated body cavity through sheath 20. Sheath 20 is inserted through the laparoscopic port 16 and provides means for deploying the entrapment envelope 22. The entrapment envelope 22 is further equipped with envelope expansion means 24 and related envelope expansion means guides 26 as shown in FIG. 3. An enlarged sectional view as presented in FIG. 3 shows the body skin line with the laparoscopic port 16 in place and the sheath 20 having a sheath cap 21 inserted therein with the entrapment envelope 22 entering the body cavity 2 through the sheath 20. Envelope expansion means 24 can be comprised of wires operating through envelope expansion mean guides 26 or in the alternative pneumatic tubing or a combination of both. In addition, the expansion means 24 can be used to assist opening the bag through stave slots or additional pneumatic tubing which are placed along the bag closed portion.

Figures 4A, 4B:
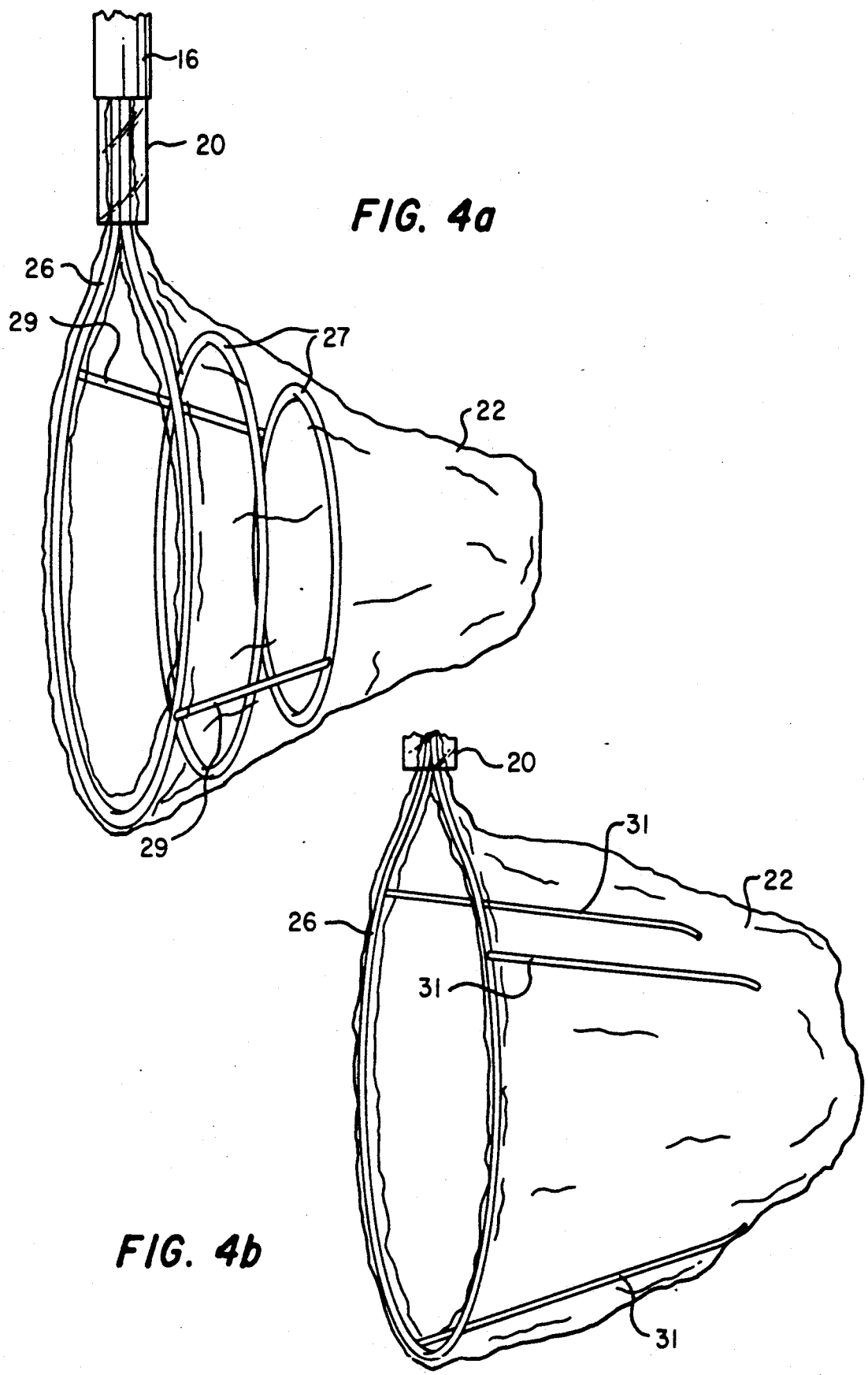
FIG. 4a is of an alternative embodiment of an enlarged view of FIG. 4 with the entrapment envelope being inserted into the body cavity and opened fully through pneumatic means for receiving surgically removed body organs.
FIG. 4b is an alternative embodiment of an enlarged sectional view in accordance with FIG. 4 with the entrapment envelope being inserted into the body cavity and opened for receiving surgically removed body organs through utilization of wire staved means or a combination of pneumatic and staved means.
Figure 5:
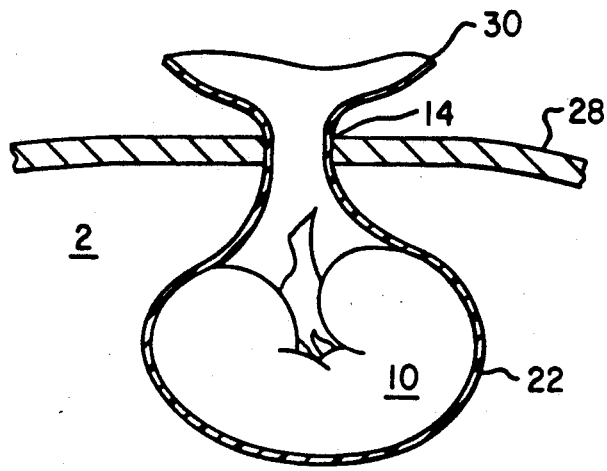
FIG. 5 is an enlarged sectional side view similar to FIGS. 3 and 4 wherein the laparoscopic port and sheath have been withdrawn with the entrapment envelope open portion being drawn through the keyhole body surgical opening in the skin after insertion of a severed kidney.
Figure 6:
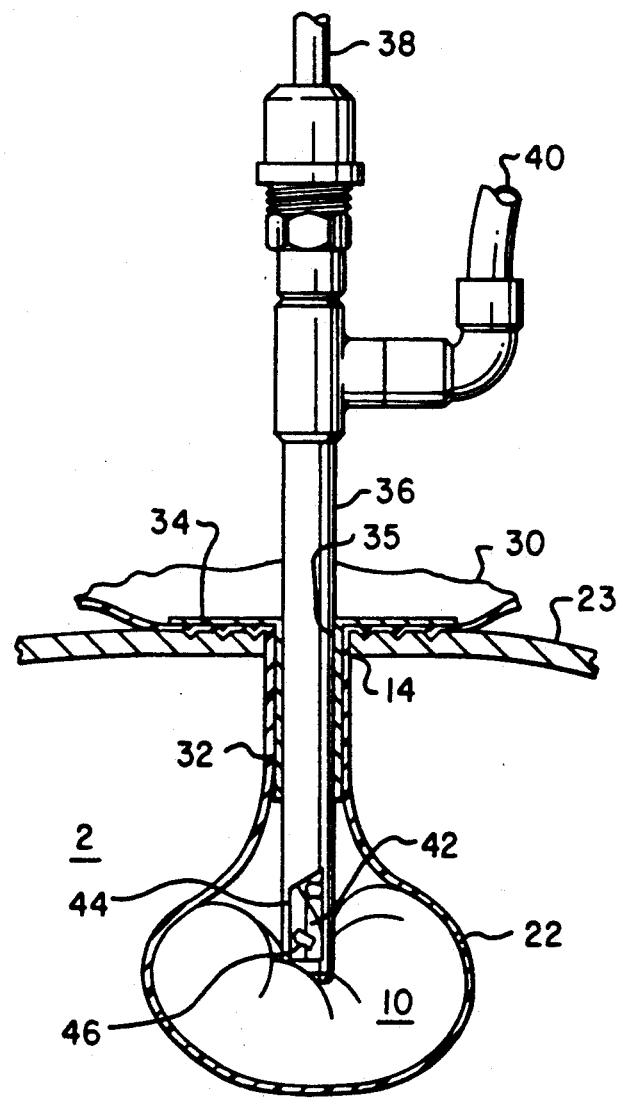
FIG. 6 is an enlarged sectional side view similar to FIG. 5 with a positioning port, entrapment envelope containing a kidney and a morsellating device inserted through the positioning port into the entrapment envelope for morsellating the kidney and removal of the particulate matter by the laparoscopic morsellator.

A related view is shown in FIG. 4 wherein an enlarged sectional view presents the entrapment envelope being fully inserted into the inflated body cavity and opened for receiving surgically removed body organs. The entrapment envelope is fully expanded with the envelope expansion mean guides being projected into a fully opened receiving mode through envelope expansion means 24. FIGS. 4a and 4b provide another embodiment of an enlarged sectional view presenting the entrapment envelope fully inserted into the inflated body cavity and opened by pneumatic or by staved means for receiving surgically removed body organs. In FIG. 4a pneumatic means are utilized for expanding the envelope expansion opening means guides 26 in communication with entrapment envelope 22 additional expansion pneumatic means 27. The pneumatic means 27 communicate with means guides 26 through tubular means 29. In FIG. 4b an alternative opening embodiment is shown utilizing expansion means guides 26 in cooperation with tubular stave means 31 in order to open the entrapment envelope 22 and assist in holding the entrapment envelope 22 in an opened position until withdrawn from the body cavity. Upon removal of the laparoscopic port 16, sheath 20, the entrapment envelope 22 is substantially closed by envelope expansion and enclosure means 24 with the entrapment envelope open end 30 being pulled through the keyhole body surgical opening 14 into position for introduction of the morsellator guide 32 having a skin gripping surface 34. The morsellation guide 32 allows and assists in entry and operation of the morsellator device 36 which is shown in operational position in FIG. 6. The positioning port 35 in combination with the morsellator device 36 provides a stop which allows the morsellator device 36 to be inserted into the body cavity a maximum, controlled distance. The expanded outer diameter of the morsellator device 36, as shown in combination with the morsellator vacuum port 40 connection, serves as a penetration depth stop for the morsellator. FIG. 6 is an enlarged sectional side view similar to FIG. 5 with a positioning port or guide 32, entrapment envelope 22 and isolated kidney 10 being particulized and removed by the laparoscopic morsellator. The morsellator device 36 contains a drive shaft 38 which is exposed for manual or mechanical drive means. The morsellator device 36 has a morsellator vacuum tissue port 40 and can utilize an irrigation port (not shown) for assisting in the removal of particulate tissue matter from the morsellator device 36. In FIG. 6 a cutting head 42 is shown with auger shaft, the morsellator device having a fenestration 44 proximal to the cutting head 42. Morsellized tissue 46 is shown being separated and fed through the morsellator device 36 having a channel in communication with morsellator vacuum tissue port 40.

Figure 7:
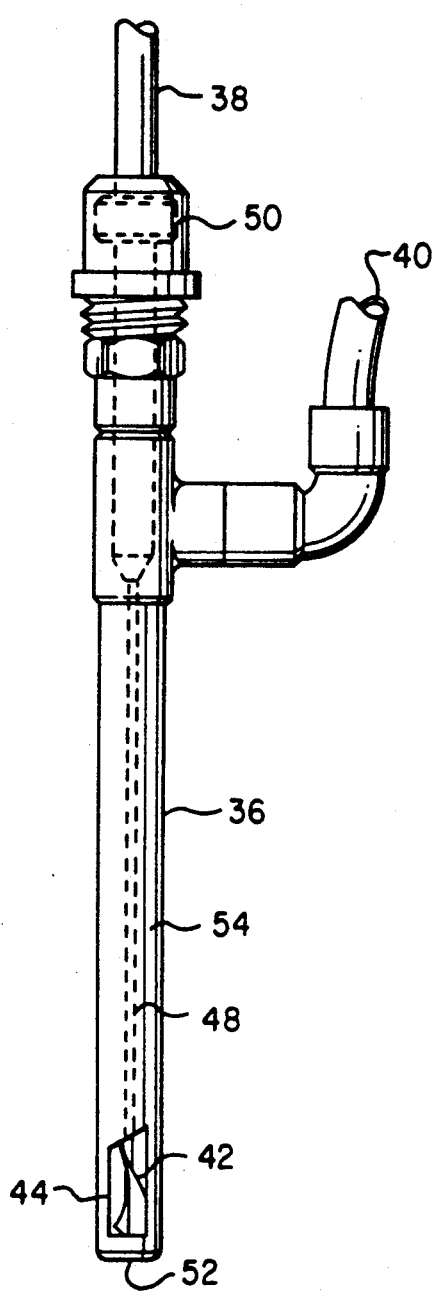
FIG. 7 is a side view of a laparoscopic morsellator in isolation utilizing one of several multiple cutter head embodiments.
Figure 8:
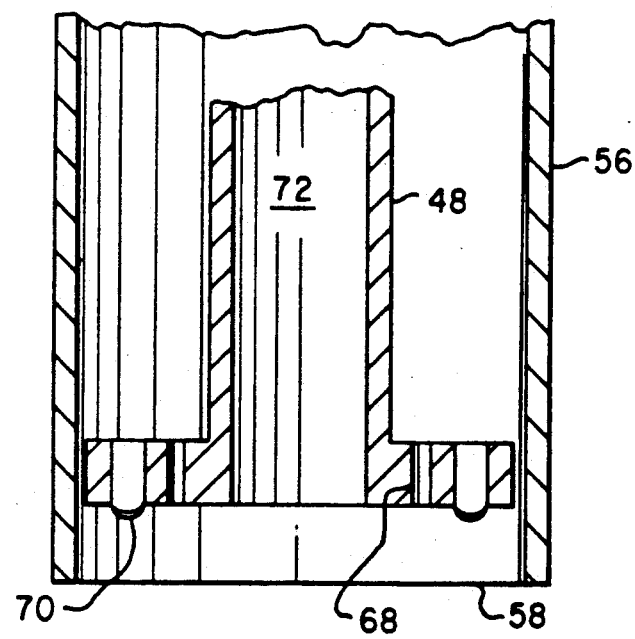
FIG. 8 is an enlarged partial section view of an open ended morsellator cutting head embodiment.

The morsellator shaft 48 as shown in FIGS. 7 and 8 is provided with a bushing 50 and a rotational shaft guide means or bearing means 52 at the morsellator device blunt, closed end. A vacuum and irrigation channel 54 provides communication between the morsellator device fenestration 44, cutting head 42 and the morsellator vacuum tissue port 40. FIG. 7 presents a side view of the laparoscopic morsellator in isolation and FIG. 8 presents an enlarged sectional view of an alternative embodiment utilizing an open-ended cutting head. The open end morsellator device head 56 as shown in FIG. 8 has an open end 58 with a cutting head 68 recessed therein. The cutting head 68 is provided with cutting elements 70 and a hollow vacuum channel 72 which pulls the organ tissue into contact with the cutting elements 70 and also provides a conduit communication for the fragmented tissue for removal through morsellator vacuum tissue port 40.

The organ entrapment envelope 22 system is comprised of several components. These components include the entrapment envelope sheath 20 and laparoscopic port 16 as illustrated in the drawings. The sheath 20 can be constructed of clear plastic construction and is of approximately the same size as the inside diameter of the laparoscopic port 16 in order that the sheath 20 fits through, for example, a 12 mm port. Depending upon the size of the organ to be retrieved, the entrapment envelope 22 and respective introduction sheath 20 will be of slightly different sizes in order to be fitted through appropriate size laparoscopic ports. In any case the keyhole body surgical opening 14 remains applicable for providing minimum invasion surgical techniques. The envelope sheath 20 can be closed at either end with closure means in order to prevent contamination of the envelope before introduction to the cavity, thus aiding in sterilization process. The envelope 22 is introduced into the sheath 20 and is prepackaged in the sheath 20 for later use. Upon introduction of the sheath 20 and the totally contained entrapment envelope 22 within the sheath 20 to the body cavity 2, the entrapment envelope 22 is totally protected from any handling damage or procedural exposure that might cause damage to the entrapment envelope 22 during the introduction through the laparoscopic port 16.

As is illustrated in the drawings, the sheath 20 extends beyond the end of the laparoscopic port 16 which again protects the entrapment envelope 22 from cutting or damage as the envelope is extruded through the end of the sheath which projects beyond the end of the port.

The distal end of the introduction sheath 20 has a perforated cap as shown in FIGS. 3 and 4 through which protrudes plastic or wire tubing which runs through the neck of the entrapment envelope in a circumferential manner. Such tubing can also be pneumatic in nature for opening of the entrapment envelope 22 and are operable through entrapment envelope 20 expansion and closure means guides 26. The guides 26 are hollow and will accommodate wires of various lengths and thicknesses to aid in the opening of the mouth of the entrapment envelope after introduction through the laparoscopic port. This introduction sheath 20 and the cap over the end of the sheath with its perforations for the plastic tubing and associated wire mechanisms or pneumatic means are of sufficient size to prevent the loss of pneumoperitoneum or the escape of gas through the introduction sheath. The wire and the plastic tubing or guides can be subsequently removed prior to actual morsellation.

Once the entrapment envelope 22 is advanced through the sheath 20 and the laparoscopic port 16, the tubing or guides 26 as well as wire aid or pneumatic aid is utilized in the advancement of the envelope through the introduction sheath and into the abdominal cavity where it can be grasped by appropriate laparoscopic graspers and further opened if needed to accommodate the placement and entrapment of the severed organ. Once the entrapment envelope 22 has been introduced into the abdomen and the organ has been placed into the entrapment envelope 22, the introduction sheath 20 is removed as well as the laparoscopic port 16. Traction is maintained on the plastic tubing/guides 26 and wire or pneumatic means to prevent the accidental dislodgement of the envelope during removal of the port 16 and sheath 20. The edges of the envelope are pulled through the keyhole surgical opening 14 in the fascia of the abdomen until the entire neck of the envelope is exteriorized. After the neck of the envelope is positioned through the skin 28, the interior of the envelope is then entered with a tissue morsellator guide 32 as shown in FIG. 6. The tissue morsellator device 36 is then advanced through the guide 32 and tissue morsellation removal commences. The tissue morsellator device guide 36 is of sufficient diameter to allow the placement of the tissue morsellator device with a small air space between the inside diameter wall of the guide and the outside wall diameter of the tissue morsellator device 36. Such dimensional relations prevent the creation of the vacuum within the organ entrapment envelope during the morsellation process. Prevention of such a vacuum prevents injury to the wall of the entrapment envelope 22 during the morsellation process. The entrapment envelope 22 according to the invention provides tubing or guides 26 relative to the neck of the envelope which have attachment means to accommodate the plastic tubing/guides 26 and wire stiffeners and/or pneumatic stiffeners.

The envelopes can be constructed of a variety of materials, including various laminated materials. However, the entrapment envelopes must be impervious to body fluids and gasses and be of reasonable low bulk and of sufficient flexibility to allow for encapsulation in the sheath and readily open from such a compressed encapsulation once inserted into the body cavity.

In one morsellator embodiment as shown in FIG. 7, an angled fenestration at an end portion of the morsellator device provides cutting access to the organ tissue while the end of the morsellator device is blunt and occluded. The tissue being morsellated is drawn into the device through the fenestration on the end portion side. The morsellator device consists of a specifically designed cutting head mounted on an auger shaft. The blunt end of the morsellator prevents the accidental passage of the cutting head beyond the end of the morsellator, thus preventing damage to the organ entrapment envelope. The cutting head auger shaft is seated in a small dimple at the end of the morsellator shaft so as to prevent wobble of the cutting head while rotating. The tissue morsellation process is aided by the application of suction or vacuum to the tissue port of the device. The application of up to about 30 inches of mercury vacuum can be applied to aid in drawing tissue into the cutting head fenestration without danger of damage to the entrapment envelope. Furthermore, the vacuum assist in evacuation of morsellated particles of tissue as particles are cut by the cutting head. An irrigation port can be added for the continuous or intermittent irrigation of the cutting head and the auger mechanism to further speed the process of tissue removal.

Morsellator shafts can be constructed of different sizes according to different types of ports and cutting heads. Various cutting heads can be utilized in accordance with the invention inclusive of recessed open-end morsellator device cutting heads in the nature of a cheese grater cutting element with a central shaft vacuum means as shown in FIG. 8. In another embodiment open end cutting heads can utilize envelope protection extensions such as an arc mean over the open end of the morsellator device containing an end cutting head. Morsellator cutting heads can be designed for specific use depending on the nature, location, diversity and size of the body part to be removed. Through the use of vacuum means for removing the morsellated tissue, the morsellation of even dense body portions removes the requirement of constant plunging to morsellate the tissue. The vacuum pulls the body portion to the morsellator cutting head.

The morsellator device for dense tissue organs such as kidneys are driven by an electric motor means which has the capacity for at least about 2,000 rpm on the drive shaft on the auger in order to provide efficient and rapid morsellation and removal of tissue. At these rpms and the sudden cutting loads on the cutting heads, bushings and appropriate fittings and other supports are necessary to prevent vibration of the morsellizer shaft. An auger type cutting head with hooked tips used in combination with an angled fenestration can also be used. The angle of the cutting auger equals the angle of the windows and the auger is useful in combination with various cutting heads for further pulverization of tissue.

An enlarged isolation view of another morsellator cutting device is shown in FIG. 9. Cutting edges 74 are relatively flat razor-type edges which terminate in upturned cutting edge tips 78. Direction of rotation is indicated by arrow 76 and such a cutting edge would be utilized in a morsellation device head similar to FIG. 8. The cutting edges 74 can be adapted with raised trailing edges 80 which assist in directing the flow of tissue and fluid away from the plane of the cut. A vacuum will be pulled as shown in FIGS. 6 and 7 through morsellizer vacuum tissue port 40 and the shaft of the morsellation device itself.

A modified morsellating device 36 is shown in FIG. 10. The morsellating device 36 of FIG. 10 is similar to the device shown in FIG. 6; however, the morsellation guide 32 utilizes bag hooks 82 for holding the bag in place during morsellation. The bag during morsellation operations has a tendency to travel back into the cavity, thus the need for such bag hooks 82. The morsellation guide 32 also is adapted with gripping teeth 84 which are in a slanted configuration for assisting in holding body tissue contained in the bag during morsellation. The body tissue has a tendency to rotate due to the various cutter head spinning actions. The morsellator head gripping teeth 86 are also effective in reducing or eliminating tissue spin. If the body part contained in the bag for morsellation removal spins, then the cutting action of the exposed cutting edges is reduced or eliminated. In another embodiment, a morsellator guide gripping pad 88 can be utilized under the morsellation guide 32 for providing additional stability of the morsellation guide during morsellation device usage.

In FIG. 11, an enlarged top perspective view of the positioning of the morsellation guide is shown in isolation. The morsellation guide 32 presents the morsellation guide bag hooks 82 with the hooks turned inward from the peripheral of the morsellation guide 32 top portion since the morsellation guide 32 is inserted into the bag opening once the bag opening has been pulled through the patient incision. Counterclockwise slanted morsellation guide gripping teeth are illustrated which hold upon contact the tissue mass which is being morsellated, preventing rotation of the mass due to the force and speed of the cutting member of the morsellation device.

A typical procedure for the laparoscopic organ retrieval of, for example, a kidney involves the surgical opening of a keyhole through which is inserted a laparoscopic port having gas communication means for inflating the body cavity with $CO_2$ or other suitable gases. The laparoscopic port allows for entry of telescope or miniature television and surgical instruments for manipulation and severing of specific organs and isolating same for introduction into an entrapment envelope. A sheath containing the entrapment envelope is inserted through the laparoscopic port and beyond the end of the laparoscopic port inside the body cavity. The entrapment envelope is then introduced to the inflated body cavity beyond the sheath opening with envelope expansion and closure means being attached to the entrapment envelope and extending through the laparoscopic port to the exterior of the body cavity. The entrapment envelope is open to receive the severed and isolated kidney which is in the body cavity. Prevention of inflation gas escaping is through utilization of dimensional relationships of the sheath and port and sheath cap means. The entrapment envelope and severed, entrapped organ is positioned upon removal of the sheath and the laparoscopic port in order to expose the opening of the entrapment envelope to the exterior of the body cavity through the keyhole incision. The entire neck of the entrapment envelope is presented to the exterior of the body cavity and a morsellizer guide is utilized in the neck of the envelope for introduction of the morsellizer device into the envelope for morsellizing and removing the kidney. Morsellized tissue is removed through vacuum and in the alternative fluid irrigation means which are in communication with the cutting head and exterior vacuum port. Upon removal of the morsellator device, the entrapment envelope and any remaining tissue therein is removed through the keyhole fascia opening.

While the invention has been illustrated and described in detail in the drawings and foregoing description, the same is to be considered as illustrative and not restrictive in character. It being understood that only exemplary embodiments have been shown and described and that all changes and modifications that come within the spirit of the invention are deemed to be protected.

We claim:

1. In a minimum invasion surgical apparatus of the type used to perform laparoscopic organ removal from a body cavity utilizing a keyhole incision which is substantially smaller than the organ, the organ being dissected from the body and isolated within the body cavity, removal of the organ from the body cavity being achieved through use of a laparoscopic port, a prepackaged compacted entrapment envelope and a moresellator means after the organ is placed in the entrapment envelope and removed by morsellation, the improvement comprising:

a sheath for insertion through the laparoscopic port into the body cavity, the sheath containing said prepackaged, compacted entrapment envelope; and said entrapment envelope constructed of flexible fluid impermeable materials having an opening and closing means extending through the port and sheath to an exterior position relative to the body cavity.

2. A minimum invasion surgical apparatus as defined in claim 1 wherein a tubular morsellator guide is inserted into the open entrapment envelope containing the organ, the morsellator guide having an inside diameter greater than the outside diameter of the morsellator means sufficient to avoid a vacuum in the entrapment envelope due to a vacuum removal means of the morsellator means.

3. A minimum invasion surgical apparatus as defined in claim 2 wherein the morsellator means has teeth means extending from a cutting head of the morsellator means.

4. A minimum invasion surgical apparatus as defined in claim 2 wherein the morsellator guide has teeth means extending from an end portion of the morsellator guide which is inserted into the entrapment envelope.

5. A minimum invasion surgical apparatus as defined in claim 2 wherein the morsellator guide has a substantially flat and enlarged circular planar portion having a first surface in contact with the exterior of the body cavity and a second surface having several inwardly turned hook devices around the circumference of the circular planar second surface for holding the entrapment envelope in place during morsellation.

6. A minimum invasion surgical apparatus as defined in claim 2 wherein the morsellator guide in combination with the morsellator means defines a penetration depth stop for the morsellator means.

7. A minimum invasion surgical apparatus as defined in claim 1 wherein the entrapment envelope opening and closing means is comprised of tubular guides around the circumference of an open portion of the envelope, said guides containing wire means for opening and closing the entrapment envelope, said wire guide means communicating with the entrapment envelope from a position exterior of the body cavity.

8. A minimum invasion surgical apparatus as defined in claim 7 wherein the entrapment envelope is further comprised of tubular stave means extending from the entrapment envelope opening circumference to form expansion loops around the perimeter of an unopened portion of the envelope.

9. A minimum invasion surgical apparatus as defined in claim 1 wherein the opening and closing means is comprised of pneumatic tubular elements which define the circumference of an open portion of the entrapment envelope and are in communication with the envelope from a position exterior of the body cavity when the envelope is inserted into the cavity said tubular means being suitable for stiffening through pneumatic means.

10. A minimum invasion surgical apparatus as defined in claim 1 wherein the entrapment envelope opening and closing means is comprised of tubular guides defining the circumference of an open portion of the entrapment envelope and is in communication with the entrapment envelope when the envelope is within the body cavity from a position exterior of the body cavity, the tubular guide means suitable for receiving a wire member in combination with pneumatic means.

11. A minimum invasion surgical apparatus as defined in claim 10 wherein the entrapment envelope is further comprised of pneumatic tubular means extending from the entrapment envelope opening circumference to form expansion loops around the perimeter of the unopened portion of the envelope.

12. A minimum invasion surgical procedure for laparoscopic organ removal from a body cavity through a keyhole body incision, comprising:

surgically opening said keyhole body incision in the abdomen;

inflating the body cavity with $CO_2$;

inserting a laparoscopic port into the keyhole incision and utilizing said keyhole incision for surgically severing an organ from the body and holding such organ in the body cavity;

inserting a sheath containing a prepackaged, compacted entrapment envelope constructed of flexible fluid impermeable materials having an opening and closing means extending through the laparoscopic port and sheath to an exterior portion relative to the body cavity through the laparoscopic port and extruding the envelope without risk of handling damage or risk of handling contamination, into the body cavity beyond the end of the laparoscopic port opening through means exterior of the body cavity;

opening the entrapment envelope utilizing said opening means;

inserting the severed organ into the entrapment envelope;

closing the entrapment envelope utilizing said closing means;

withdrawing the sheath;

withdrawing the laparoscopic port;

withdrawing the open portion of the entrapment envelope to an exterior position of the body cavity;

introducing morsellizing means into the open end of the entrapment envelope;

morsellizing and removing the severed organ from the envelope; and removing the entrapment envelope and remaining tissue from the body cavity through the keyhole incision.

13. The minimum invasion surgical procedure for laparoscopic organ removal according to claim 12 wherein a morsellator guide is inserted into the withdrawn open portion of the entrapment envelope before introduction of the morsellizing means.

14. The minimum invasion surgical procedure for laparoscopic organ removal according to claim 12 wherein the opening of the entrapment envelope is through pneumatic tubing means.

15. The minimum invasion surgical procedure for laparoscopic organ removal according to claim 12 wherein the opening of the entrapment envelope is through wire guide and wire means.

16. The minimum invasion surgical procedure for laparoscopic organ removal according to claim 12 wherein the procedure is comprised of laparoscopic cholecystectomy.

17. The minimum invasion surgical procedure for laparoscopic organ removal according to claim 12 wherein the procedure is comprised of laparoscopic nephrectomy.

18. In a minimum invasion surgical apparatus of the type used to perform laparoscopic organ removal from a body cavity utilizing a keyhole incision which is substantially smaller than the organ, the organ being dissected from the body and isolated within the body cavity, removal of the organ from the body cavity being achieved through use of a laparoscopic port, an entrapment envelope and a morsellator means after the organ is placed in the entrapment envelope and removed by morsellation, the improvement comprising:

a sheath for insertion through the laparoscopic port into the body cavity, the sheath containing a prepackaged, compacted entrapment envelope;

said entrapment envelope being constructed of flexible fluid impermeable materials having an opening and closing means communicating through the port and sheath to an exterior position relative to the body cavity; and the sheath is provided with a cap on a first end which is exterior of the body cavity during insertion of the entrapment envelope through a second end which accommodates the opening/closing means, the cap provides a pressure seal to the sheath, the sheath outer diameter sufficiently similar to the inside diameter of the laparoscopic port to avoid significant body cavity gas pressure loss.

* * * * *